(12) United States Patent
Brase et al.

(10) Patent No.: US 7,244,150 B1
(45) Date of Patent: Jul. 17, 2007

(54) CONNECTOR AND METHODS OF FABRICATION

(75) Inventors: Randall Lee Brase, Castaic, CA (US); Robert Randall Tong, Valencia, CA (US)

(73) Assignee: Advanced Bionics Corporation, Valencia, CA (US)

( * ) Notice: Subject to any disclaimer, the term of this patent is extended or adjusted under 35 U.S.C. 154(b) by 0 days.

(21) Appl. No.: 11/327,880

(22) Filed: Jan. 9, 2006

(51) Int. Cl.
*H01R 13/64* (2006.01)

(52) U.S. Cl. .................. 439/668; 439/909; 607/37; 607/46

(58) Field of Classification Search .......... 439/668, 439/669, 909, 23–26, 28; 607/37, 46
See application file for complete search history.

(56) References Cited

U.S. PATENT DOCUMENTS

| | | | | |
|---|---|---|---|---|
| 3,601,747 | A | * | 8/1971 | Prall et al. ............. 439/26 |
| 3,718,142 | A | | 2/1973 | Muller |
| 3,771,106 | A | * | 11/1973 | Matsumoto et al. ...... 439/23 |
| 4,003,616 | A | * | 1/1977 | Springer ................. 439/23 |
| 4,364,625 | A | * | 12/1982 | Baker et al. ............ 439/188 |
| 4,367,907 | A | * | 1/1983 | Buck ..................... 439/188 |
| 4,695,116 | A | * | 9/1987 | Bailey et al. ........... 439/188 |
| 4,695,117 | A | * | 9/1987 | Kysiak .................. 439/188 |
| 4,712,557 | A | * | 12/1987 | Harris ................... 607/37 |
| 4,867,708 | A | * | 9/1989 | Iizuka ................... 439/668 |
| 5,193,539 | A | | 3/1993 | Schulman et al. |
| 5,193,540 | A | | 3/1993 | Schulman et al. |
| 5,312,439 | A | | 5/1994 | Loeb |
| 5,435,731 | A | * | 7/1995 | Kang .................... 439/26 |
| 6,051,017 | A | | 4/2000 | Loeb et al. |
| 6,181,969 | B1 | * | 1/2001 | Gord .................... 607/59 |
| 6,516,227 | B1 | * | 2/2003 | Meadows et al. ........ 607/46 |
| 6,604,283 | B1 | | 8/2003 | Kuzma |
| 6,609,029 | B1 | * | 8/2003 | Mann et al. ............ 607/37 |
| 6,609,032 | B1 | * | 8/2003 | Woods et al. ........... 607/46 |
| 6,741,892 | B1 | | 5/2004 | Meadows et al. |
| 6,757,970 | B1 | | 7/2004 | Kuzma et al. |
| 2004/0059392 | A1 | | 3/2004 | Parramon et al. |

FOREIGN PATENT DOCUMENTS

| | | |
|---|---|---|
| WO | WO-98/37926 | 9/1998 |
| WO | WO-98/43700 | 10/1998 |
| WO | WO-98/47301 | 10/1998 |

OTHER PUBLICATIONS

U.S. Appl. No. 11/238,240, "Implantable Stimualtor with Integrated Plastic Housing/Metal Contacts and Manufacture and Use," Applicants He, T. X. et al., filed Sep. 29, 2005.

* cited by examiner

*Primary Examiner*—Gary F. Paumen
(74) *Attorney, Agent, or Firm*—Darby & Darby P.C.; Bruce E. Black (57) ABSTRACT

A connector includes a unitary body defining a hollow center region configured and arranged to receive a proximal contact portion of a lead. The unitary body may define connector pockets and seal features within the hollow center region. The connector pockets can be spaced-apart and may define openings through the unitary body. The seal features may be disposed between the connector pockets.

20 Claims, 5 Drawing Sheets

CONNECTOR AND METHODS OF FABRICATION

FIELD OF THE INVENTION

The invention is directed to stimulators and stimulator components and methods of making the devices. The invention is also directed to stimulators and stimulator components with a connector, as well as methods of making the devices.

BACKGROUND OF THE INVENTION

Stimulators have been developed to provide therapy for a variety of disorders, as well as for other treatments. For example, stimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

As one example, spinal cord stimulation is a well accepted clinical method for reducing pain in certain populations of patients. Stimulators have been developed to provide therapy for a variety of treatments. For example, stimulators can be used to stimulate nerves, such as the spinal cord, muscles, or other tissue. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

BRIEF SUMMARY OF THE INVENTION

In one embodiment, a connector includes a unitary body defining a hollow center region configured and arranged to receive a proximal contact portion of a lead. The unitary body further defines within the hollow center region a plurality of spaced-apart connector pockets. Each connector pocket defines an opening through the unitary body. The unitary body further defines within the hollow center region a plurality of seal features disposed between the connector pockets.

In another embodiment, a stimulation device includes a lead with a proximal contact portion comprising a plurality of contacts, an electronic subassembly, a connector, and a plurality of conductive contacts. The connector receives the proximal contact portion of the lead. The connector includes a unitary body that defines a hollow center region configured and arranged to receive the proximal contact portion of the lead. The unitary body further defines within the hollow center region a plurality of spaced-apart connector pockets. Each connector pocket defines an opening through the connector. The unitary body further defines within the hollow center region a plurality of seal features disposed between the connector pockets. The conductive contacts are disposed in the openings of the connector and are configured and arranged to couple the contacts of the lead to the electronic subassembly.

In another embodiment, a method of making a stimulation device includes forming a connector, disposing a plurality of conductive contacts in the openings through the unitary body, and coupling contacts on a lead to an electronic subassembly through the connector and conductive contacts. The connector includes a unitary body defining a hollow center region configured and arranged to receive a proximal contact portion of a lead. The unitary body further defines within the hollow center region a plurality of spaced-apart connector pockets. Each connector pocket defines an opening through the unitary body. The unitary body further defines within the hollow center region a plurality of seal features disposed between the connector pockets.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION OF THE INVENTION

The invention is directed to stimulators and stimulator components and methods of making the devices. The invention is also directed to stimulators and stimulator components with a connector, as well as methods of making the devices.

Examples of stimulators are found in U.S. Pat. Nos. 6,181,969; 6,516,227; 6,609,029; 6,609,032; and 6,741,892; and U.S. patent application Ser. No. 11/238,240, all of which are incorporated by reference.

In at least some applications, the electronic subassembly of a stimulator is coupled to the lead, which includes the electrodes of the stimulator. In at least some designs, the lead has several contacts that connect to individual connector contacts via a connector. The connector contacts may be arranged, for example, in a single row, and are generally electrically isolated from each other.

In at least some designs, the spacing and pitch between the individual contacts may vary due to variation in manufacturing processes or components. Such variation can result in misalignment between the contacts of the lead and the individual connector contacts. To address this, in one embodiment, a connector having a unitary body with periodically spaced connector contacts electrically isolates the connections between adjacent pairs of lead contacts and connector contacts. For example, the connector can include spaced-apart connector pockets into which conductive contacts may be inserted.

As one example, a connector includes a unitary body that defines a hollow center region configured and arranged to receive a proximal contact portion of a lead. The unitary body further defines within the hollow center region spaced-apart connector pockets, where each connector pocket defines an opening through the unitary body. Conductive contacts can be disposed in the openings through the unitary body.

Figure 2:
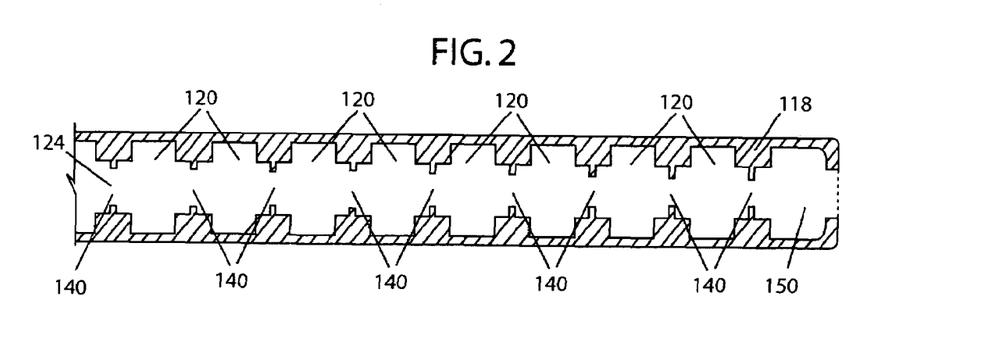
FIG. 2 is a schematic cross-sectional view of the unitary body of the connector of FIG. 1.

FIG. 2 illustrates schematically a cross-sectional view of one embodiment of a unitary body 118 of a connector, according to the invention. The unitary body 118 defines a hollow center region 124 that is capable of receiving the proximal contact portion of a lead. Suitable materials for the unitary body 118 include, for example, silicone and polyurethane. In some instances, the unitary body 118 may be formed from more than one material.

The unitary body 118 further defines connector pockets 120 within the hollow center region 124. The unitary body 118 may include any number of connector pockets 120. There may be, for example, two, three, four, five, six, seven, eight, nine, ten, eleven, twelve, thirteen, fourteen, fifteen, sixteen, seventeen, eighteen, or more connector pockets 120. Preferably, the number of connector pockets 120 is equal to the number of contacts on the proximal contact portion of the lead.

Figure 3:
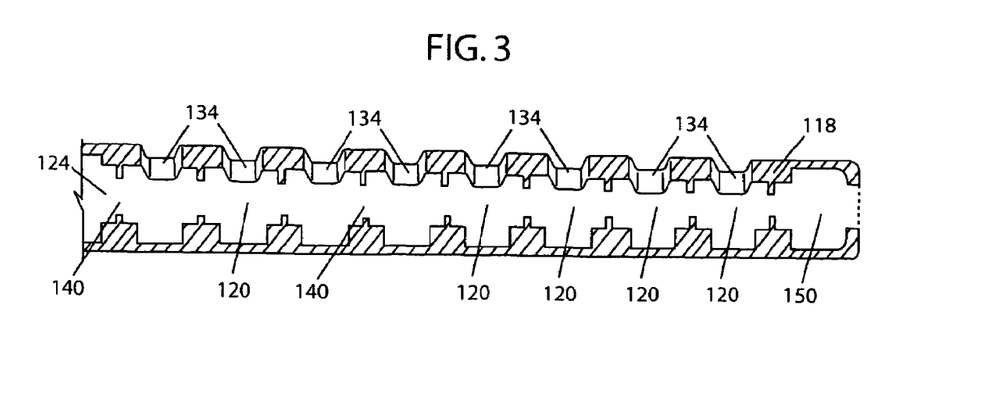
FIG. 3 is a schematic cross-sectional view of the unitary body of the connector of FIG. 1 from a different side.

In one embodiment illustrated in FIG. 3, the connector pockets 120 define an opening 134 through the unitary body 118. The openings 134 through the unitary body 118 may be located on any side of the unitary body 118. Preferably, the openings 134 are all located on the same side of the unitary body 118.

The connector pockets 120 are spaced-apart. The connector pockets 120 may be spaced-apart in any fashion. For example, the connector pockets 120 can be regularly (e.g., with a regular period) spaced-apart. In one embodiment, the connector pockets 120 are spaced-apart at substantially uniform intervals. Preferably, the connector pockets 120 are spaced-apart such that the openings 134 defined by the connector pockets 120 can be aligned with the lead contacts of the proximal contact portion of the lead received by the unitary body 118.

Figure 1:
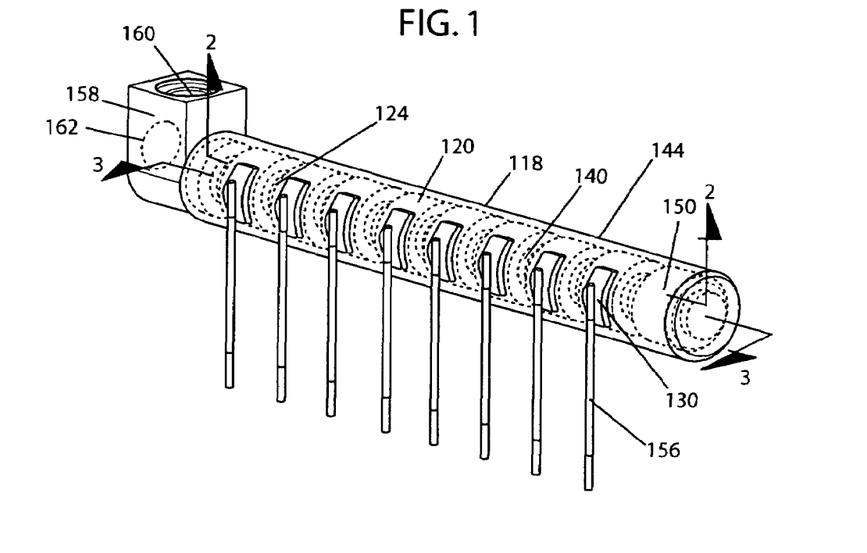
FIG. 1 is a schematic perspective view of one embodiment of a connector, according to the invention.

The opening 134 through the unitary body 118 may have any dimensions. Preferably, the opening 134 is capable of receiving a conductive contact 130 (FIG. 1). Conductive contacts 130 may be made of any material that is conductive including, for example, metals, alloys, conductive polymers, conductive carbon, etc. There may be any number of conductive contacts including, for example, two, three, four, five, six, seven, eight, nine, ten, eleven, twelve, thirteen, fourteen, fifteen, sixteen, seventeen, eighteen or more conductive contacts 130. Preferably, the number of conductive contacts 130 is equal to the number of connector pockets 120.

The conductive contacts 130 couple the electronic subassembly 110 (FIG. 4) to the lead 106 (FIG. 4) through the conductors 156 (FIG. 1). Optionally, the conductors 156 may be insulated by an insulating material except where the conductor 156 makes contact with the conductive contacts 130, electronic subassembly 110, or other components of the electrical circuitry. The insulating material may be any material that is a poor conductor of an electrical signal including, for example, Teflon™, and non-conductive polymers.

In one embodiment, the unitary body 118 further defines within the hollow center region 124 a stop pocket 150 (FIG. 2). The stop pocket 150 is located at the end of the unitary body 118 opposite the end from which the lead is inserted.

In one embodiment, the unitary body 118 is coupled to a connector block 158 as illustrated, for example, in FIG. 1. The connector block 158 can be made of any conductive or non-conductive material. Suitable non-conductive materials for the connector block 158 include, for example, non-conductive polymers, polyetheretherketone (PEEK), ceramics, etc. Suitable conductive materials include, but are not limited to, metal, alloys, conductive polymers, conductive carbon, etc.

In one embodiment, the connector block 158 aids positioning and/or securing the proximal contact portion of the lead within the hollow center region 124 of the unitary body 118. In one embodiment, the connector block 158 has an insertion opening 162 through which the proximal portion of the lead may pass (FIG. 1). The connector block 158 may also have a securement opening 160 that may be used to secure the proximal contact portion of the lead disposed within the hollow center region 124 of the unitary body 118 (FIG. 1). Optionally, the securement opening 160 may be roughly perpendicular to the insertion opening 162 (FIG. 1). A pin, screw or other member can be inserted through the securement opening 160 in the connector block 158 to secure the proximal contact portion of the lead in the hollow center region 124 of the unitary body 118.

The connector block 158 may be coupled to any end of the unitary body 118. Preferably, the connector block 158 is coupled to the end of the unitary body 118 that is opposite the end of the unitary body 118 where the stop pocket 150 is located.

In one embodiment, the unitary body 118 further defines seal features 140 (FIG. 2) within the hollow center region 124. The seal features 140 are located between the connector pockets 120. A seal feature(s) 140 may also be disposed between a connector pocket 120 and a stop pocket 150.

The unitary body 118 may include any number of seal features 140. There may be, for example, two, three, four, five, six, seven, eight, nine, ten, eleven, twelve, thirteen, fourteen, fifteen, sixteen, seventeen, eighteen or more seal features 140. For example, one seal feature 140 is disposed between each pair of adjacent connector pockets 120. A seal feature 140 may also be disposed between a connector pocket 120 and a connector block 158. Preferably, the number of seal features 140 is one greater than the number of conductive contacts 130.

The seal features 140 generally electrically isolate electrical circuitry located in each connector pocket 120 from the electrical circuitry located in other connector pockets 120. For example, the seal features 140 may electrically isolate each connection between a conductive contact 130 and a lead contact of the lead received by the unitary body 118.

Figure 4:
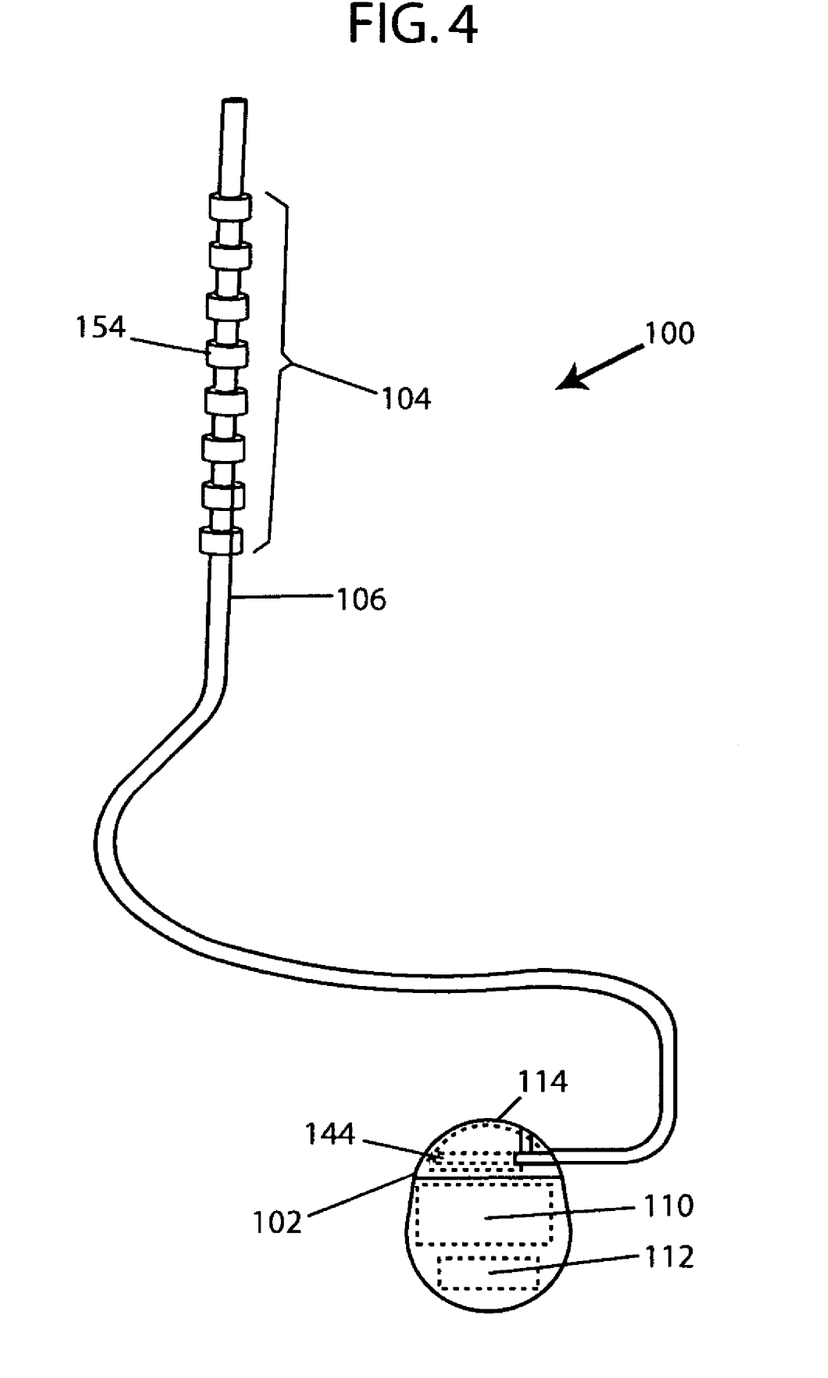
FIG. 4 is a schematic exterior perspective view of one embodiment of a stimulator system, according to the invention.

FIG. 4 illustrates schematically one embodiment of a stimulation system 100. The stimulation system includes a control module (e.g., a stimulator or pulse generator) 102, an electrode array 104, and at least one lead body 106 coupling the control module to the electrode array. The electrode array 104 and the lead body 106 form a lead. Examples of leads include, for example, percutaneous leads and paddle leads. It will be understood that the system for stimulation can include more, fewer, or different components and can have a variety of different configurations including those configurations disclosed in the stimulator references cited herein. The stimulation system or components of the stimulation system, including one or more of the lead body 106, electrode array 104, and the control module 102, may be implanted into the body.

The control module 102 typically includes a housing 114 with an electronic subassembly 110 and, in at least some embodiments, a power source 112 disposed within a chamber in the housing. Preferably, the housing is resistant to moisture penetration into the chamber containing the electronic subassembly and power source. In some embodiments, water may diffuse through the housing. Preferably, the diffused water is relatively pure, without substantial ionic content, as deionized water is relatively non-conductive.

The housing 114 may be made of any biocompatible material including, for example, glass, ceramics, metals, epoxies and polymers (including plastics). In one embodiment, the housing 114 of the control module is formed of a plastic material that resists the transport of moisture into the interior of the housing and is sufficiently sturdy to protect the components on the interior of the housing from damage under expected usage conditions. Preferably, the material of the plastic housing is a hydrophobic polymer material.

The housing 114 may include additives such as, for example, fillers, plasticizers, antioxidants, colorants, and the like. The thickness of the walls of the housing may also impact the moisture permeability of the housing. A minimum thickness needed to achieve a particular degree of resistance to moisture transport will often depend on the material selected for the housing, as well as any additives.

Optionally, the housing 114 can be covered, in full or in part, with a coating. The coating can be provided to improve or alter one or more properties of the housing 114 including, for example, biocompatibility, hydrophobicity, moisture permeability, leaching of material into or out of the housing, and the like. In one embodiment, a coating can be applied which contains a compound, such as, for example, a drug, prodrug, hormone, or other bioactive molecule, that can be released over time when the stimulator is implanted. (In another embodiment, the housing itself may include such a compound to be released over time after implantation.)

The connector 144 is disposed in a portion of the housing that is, at least initially, not sealed. This allows the proximal end of the lead 106 to be inserted into the unitary body 118 of the connector 144. The conductors 156 (FIG. 1), or other electrical conduits (not shown) attached to the conductors 156, penetrate the housing 114 into the sealed chamber containing the electronic subassembly 110, and are attached to the electronic subassembly 110.

Figure 5:
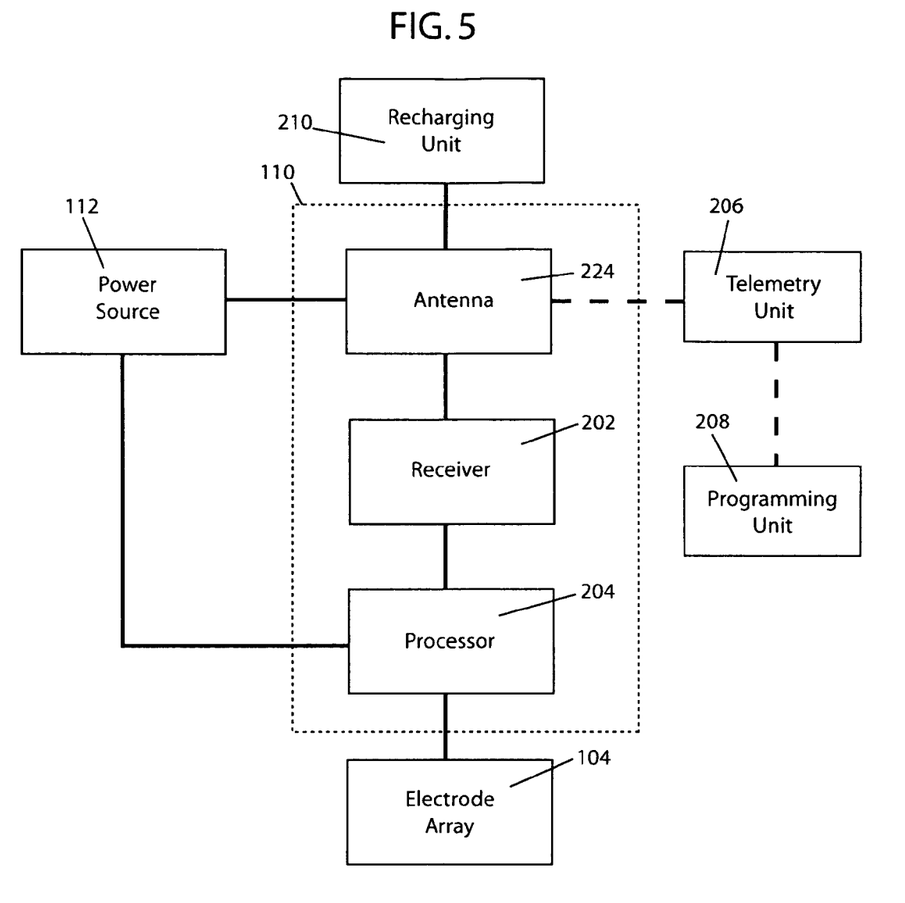
FIG. 5 is a schematic overview of components of a system for stimulation, according to the invention.
Figure 6:
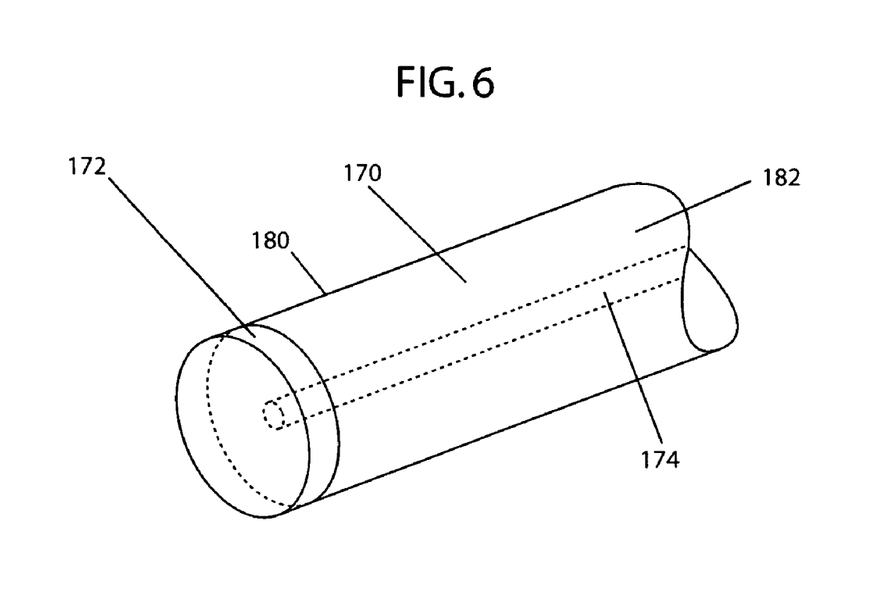
FIG. 6 is a schematic perspective view of one embodiment of a mold frame, an end pin and a locating feature, according to the invention.

FIG. 5 is a schematic overview of one embodiment of components of a system for stimulation, including an electronic subassembly 110 (which may or may not include the power source 112), according to the invention. It will be understood that the system for stimulation and the electronic subassembly 110 can include more, fewer, or different components and can have a variety of different configurations including those configurations disclosed in the stimulator references cited herein. Some or all of the components of the system for stimulation can be positioned on one or more circuit boards or similar carriers within a housing of a stimulator, if desired.

Any power source 112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. patent application Publication No. 2004/0059392, incorporated herein by reference.

As another alternative, power can be supplied by an external power source through inductive coupling via the optional antenna 224 or a secondary antenna. The external power source can be in a device that is mounted on the skin of the user or in a unit that is provided near the stimulator user on a permanent or periodic basis.

If the power source 112 is a rechargeable battery, the battery may be recharged using the optional antenna 224, if desired. Power can be provided to the battery for recharging by inductively coupling the battery through the antenna to a recharging unit 210 (see FIG. 5) external to the user. Examples of such arrangements can be found in the stimulator references identified above.

In one embodiment, electrical current is emitted by the electrodes 154 to stimulate motor nerve fibers, muscle fibers, or other body tissues near the stimulator. The electronic subassembly 110 provides the electronics used to operate the stimulator and generate the electrical pulses at the electrodes 154 to produce stimulation of the body tissues. FIG. 5 illustrates one embodiment of components of the electronic subassembly and associated units.

In the illustrated embodiment, a processor 204 is generally included in the electronic subassembly 110 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 224. This allows the processor to receive instructions from an external source to direct the pulse characteristics and the selection of electrodes, if desired.

In one embodiment, the antenna 224 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 224 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 110 does not include an antenna 224 or receiver 202 and the processor 204 operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 224 can have any form. In one embodiment, the antenna comprises a coiled wire that is wrapped at least partially around the electronic subassembly within or on the housing.

Any method of manufacture of the components of the system for stimulation can be used. For example, the power source and antenna can be manufactured as described in U.S. patent application Publication No. 2004/0059392. These components can then be placed inside the housing (or, alternatively, the housing can be formed, e.g., molded, around the components).

In one embodiment, a method of making a stimulation device includes forming a connector 144 comprising a unitary body 118 and coupling a lead 106 to an electronic subassembly 110 through the connector 144. The unitary body 118 of the connector 144 may be formed by any method that results in the unitary body 118 defining a hollow center region 124 capable of receiving a proximal contact portion of a lead. The unitary body 118 is formed such that the unitary body 118 defines connector pockets 120 within the hollow center region 124. The unitary body 118 may be formed, for example, by molding (including injection molding), casting, etc.

As an example, the unitary body 118 can be formed by molding. In one embodiment, an end pin 172 is inserted onto one end of a mold frame 170 as illustrated schematically in FIG. 10. Suitable materials for the mold frame 170 include, but are not limited to, metal, wood, wax, polymers, and the like. Preferably, the mold frame 170 is made of a material such that the mold frame 170 is reusable.

Figure 10:
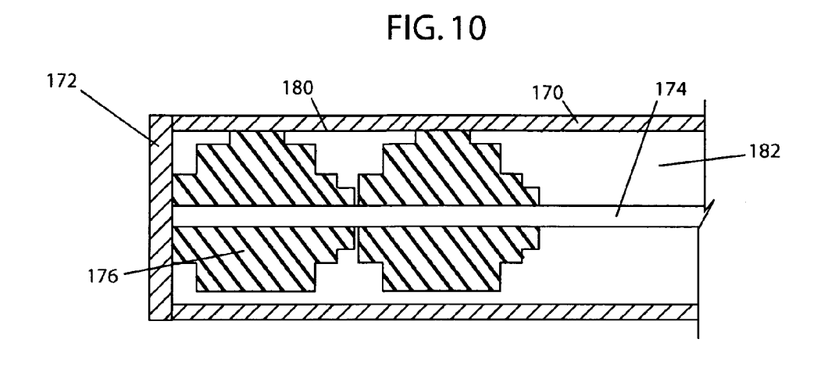
FIG. 10 is a schematic cross-sectional view of one embodiment of mold insert pieces disposed in a mold frame, according to the invention.

The interior surface 180 of the mold frame 170 is generally complementary to the desired external shape of the unitary body 118. Preferably, the unitary body 118 has a cylindrical exterior shape. The interior surface 180 of the mold frame 170 typically defines the dimensions of the exterior of the unitary body 118. Preferably, the mold frame 170 has at least one open surface 182, which may optionally be sealed with an end pin 172. Optionally, the final molded unitary body 118 can be removed from the mold frame 170 through the at least one open surface 182 of the mold frame 170.

Suitable materials for the end pin 172 include, but are not limited to, metals, wood, wax, polymers, and the like. Preferably, the end pin 172 is made of a material such that the end pin 172 is reusable. The end pin 172 may have any shape or dimensions. Preferably, the end pin 172 has a shape and dimensions such that the end pin 172 may seal an open surface 182 of the mold frame 170. The end pin may also have a shape of a stop pocket 150 or a connector pocket 120.

Figure 11:
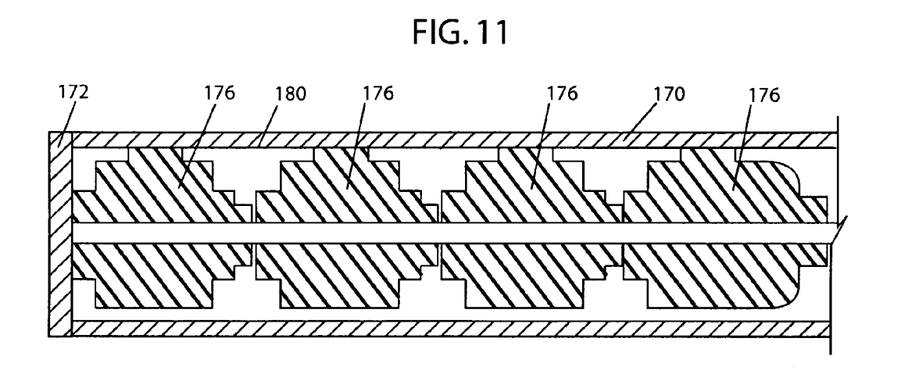
FIG. 11 is a schematic cross-sectional view of one embodiment of mold insert pieces disposed in a mold frame, according to the invention.

In one embodiment, at least one mold insert piece 176 is disposed within the mold frame 170 (see FIGS. 10 and 11). Suitable materials for the mold insert piece 176 include, but are not limited to, metals, wood, wax, polymers, and the like. Preferably, the mold insert piece 176 is made of a material such that the mold insert piece 176 is reusable. In one embodiment, a single mold insert piece 176 is disposed within the mold frame 170. Optionally, two, three, four, five, six, seven, eight, nine, ten, eleven, twelve, thirteen, fourteen, fifteen, sixteen, seventeen, eighteen, or more mold insert pieces 176 can be disposed within the mold frame 170.

Figure 7:
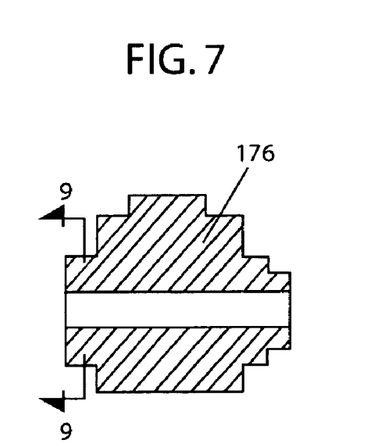
FIG. 7 is a schematic cross-sectional view of one embodiment of a mold insert piece, according to the invention.
Figure 8:
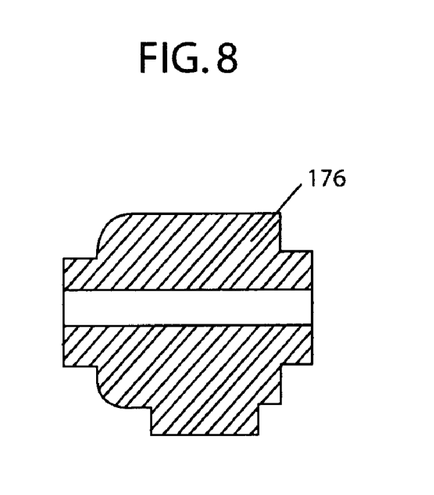
FIG. 8 is a schematic cross-sectional view of one embodiment of a mold insert piece, according to the invention.

In one embodiment, the mold insert pieces 176 have a shape such that the cumulative shape of all the mold insert pieces 176 disposed within the mold frame 170 defines the desired shape of the hollow center region 124 of the unitary body 118. In one embodiment, the mold insert pieces 176 have a shape such that, when the mold insert pieces 176 are located in the mold frame 170, the exterior surface of the combined mold insert pieces 176 defines the connector pockets 120, seal features 140, and stop pockets 150, if any, of the unitary body 118 as illustrated schematically in FIGS. 7 and 8. It will be recognized that, optionally, the end pins 172 can also have the shape of a stop pocket 150 or other mold insert piece 176.

Figure 9:
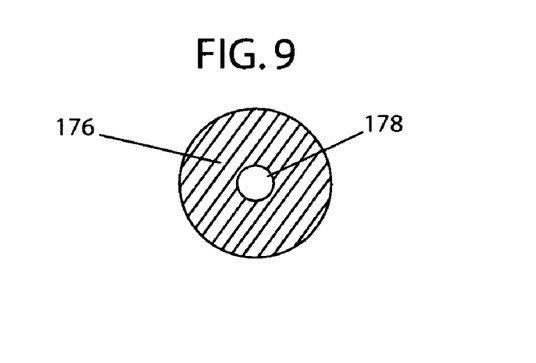
FIG. 9 is a schematic end cross-sectional view of the mold insert piece of FIG. 7.

In one embodiment, the mold insert pieces 176 may be located and/or secured into position within the mold frame 170 by one or more locating features 174. The locating features 174 may be anything that aids positioning of the mold insert pieces 176 within the mold frame 170 or that aids in securing the position of the mold insert pieces 176 once they are disposed in the mold frame 170. For example, a cylindrical rod disposed within the mold frame 170 may act as a locating feature 174 as illustrated schematically in FIGS. 8, 12, and 13. Optionally, a positioning aperture 178 disposed within a mold insert piece 176 may act as a locating feature 174. In one embodiment, a positioning aperture 178 locating feature 174 is illustrated schematically in FIG. 9. Other locating features can include pins in one end of the mold insert piece 176 (or end pin 172) that correspond with holes in the end of another mold insert piece 176 (or end pin 172).

In one embodiment, cooperating locating features 174 may aid in disposing or securing mold insert pieces 176 in the mold frame 170. For example, a cylindrical rod locating feature 174 may act cooperatively with a positioning aperture 178 locating feature 174 disposed within a mold insert piece 176. In one embodiment, the positioning aperture 178 disposed within mold insert pieces 176 may be used to thread the mold insert pieces 176 onto the cylindrical rod locating feature 174. Pins/holes in the end of the mold insert pieces may also aid in aligning the opening 134—creating features.

Figure 12:
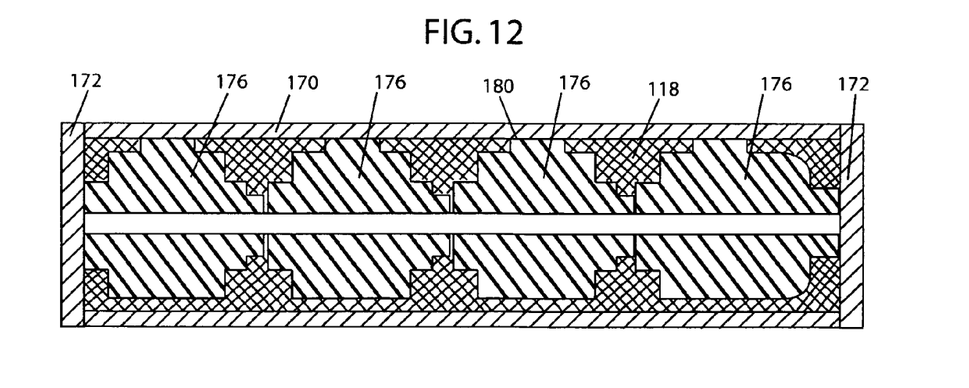
FIG. 12 is a schematic cross-sectional view of one embodiment of a unitary body molded around mold insert pieces disposed within a mold frame, according to the invention.

After disposing the mold insert piece(s) 176 in the mold frame 170, at least one end pin 172 can be used to seal an open surface 182 of the mold frame 170 as illustrated schematically in FIG. 12.

A material suitable for forming the unitary body 118 is then added into the mold frame 170 containing the mold insert pieces 176. For example, the material suitable for forming the unitary body 118 may be injected into the mold frame 170. This material may then be allowed to cure, harden, or otherwise solidify. In one embodiment, a polymerizing agent may be added to the material to facilitate curing.

Once the unitary body 118 material has cured, hardened, or otherwise solidified, at least one end pin 172 (and in some instances, two end pins) is removed. In some instances, the unitary body 118 is temporarily deformed (e.g., stretched) to remove one or more of the end pins 172. In some embodiments, locating features 174 may also be removed at this time. For example, a cylindrical rod locating feature 174 that passes through positioning apertures 178 of the mold insert pieces 176 may be removed at this time.

In some embodiments, the unitary body 118 is removed from the mold frame 170. In one embodiment, the mold insert pieces 176 are then removed from the unitary body 118. The mold insert pieces 176 may be removed from the unitary body 118 in any manner. Optionally, removal of the mold insert pieces 176 may be aided by altering the properties of the material used to form the unitary body 118. For example, the unitary body 118 may be formed from polysilicone and the polysilicone unitary body 118 may be swollen by treating the polysilicone with hexane or another material that swells the polysilicone. The swelling of the polysilicone unitary body 118 may facilitate removal of the mold insert pieces 176 through the openings 134 in the unitary body 118. The openings may be temporarily deformed (e.g., stretched) during this process. In such instances, it is preferable that the unitary body 118 be made of a suitable material which allows such deformation and then returns to its original shape.

Once the mold insert pieces 176 are removed, the conductive contacts 130 are disposed within the connector pockets 120. The conductive contacts 130 may be disposed within the connector pockets 120 in any manner. Optionally, disposing the conductive contacts 130 in the connector pockets 120 may also be aided by altering the properties of the material used to form the unitary body 118. For example, the unitary body 118 may be formed from polysilicone. The polysilicone unitary body 118 may be swollen by treatment with hexane or another material that swells the polysilicone. The conductive contacts 130 may then be disposed within the connector pockets 120 of the unitary body 118. As the polysilicone is allowed to dry, the swelling of the polysilicone unitary body 118 decreases, and the conductive contacts 130 are disposed within the polysilicone as the polysilicone shrinks around the conductive contacts 130. Optionally, adhesive may be used to further attach the conductive contacts 130 to the unitary body 118.

Conductors 156 may then be coupled to the conductive contacts 130 by any suitable method including, for example, welding, soldering, and the like. Optionally, the conductors 156 may be attached to electrical conduits (not shown) that pass through the housing 114 to the sealed chamber.

In one embodiment, the connector 144 includes a connector block 158 coupled to the unitary body 118. The unitary body 118 may be coupled to the connector block 158 by any method that results in the unitary body 118 remaining coupled to the connector block 158 under expected usage conditions. For example, the unitary body 118 may be coupled to the connector block 158 using an adhesive. Suitable adhesives include, for example, silicones, epoxies, and acrylics. Optionally, the unitary body 118 may be coupled to the connector block 158 using a fastening device such as, for example, a screw, pin, etc.

Upon completion, the connector 144 can be permanently or removably disposed in the housing 114 of the control module 102. The proximal end of the lead body 106 is inserted into the connector 144 prior to or during implantation and optionally secured using the connector block 158. Adhesive or other material may be added to the connector/lead assembly to more securely attach the proximal end of the lead body 106 to the connector 144 or seal the interior of the connector 144 from contact with body fluids.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector comprising:
    a unitary body defining a hollow center region configured and arranged to receive a proximal contact portion of a lead, the unitary body further defining within the hollow center region a plurality of spaced-apart connector pockets, wherein each connector pocket defines an opening through the unitary body, and the unitary body further defining within the hollow center region a plurality of seal features disposed between the connector pockets, the connector pockets adapted to receive a plurality of conductive contacts entirely therein except for a part, if any, of the contacts which protrude through the openings.

2. The connector of claim 1, wherein the openings through the unitary body are disposed on one side of the unitary body.

3. The connector of claim 1, wherein the connector pockets are spaced-apart at substantially uniform intervals.

4. The connector of claim 1, wherein the unitary body further defines a stop pocket at an end of the hollow center region.

5. The connector of claim 1, further comprising a connector block coupled to the unitary body.

6. The connector of claim 1, further comprising the plurality of conductive contacts disposed in the openings through the unitary body.

7. The connector of claim 6, further comprising a plurality of conductors coupled to the conductive contacts.

8. The connector of claim 1, wherein the unitary body comprises polysilicone.

9. The connector of claim 1, wherein at least four conductive contacts are disposed in the openings through the unitary body.

10. A stimulation device comprising:
    a lead with a proximal contact portion comprising a plurality of contacts;
    an electronic subassembly;
    a connector that receives the proximal contact portion of the lead, wherein the connector comprises a unitary body that defines a hollow center region configured and arranged to receive the proximal contact portion of the lead, wherein the unitary body further defines within the hollow center region a plurality of spaced-apart connector pockets, wherein each connector pocket defines an opening through the connector, and the unitary body further defining within the hollow center region a plurality of seal features disposed between the connector pockets and entirely in the connector pockets except for a part, if any, of the contacts which protrude through the openings; and a plurality of conductive contacts disposed in the openings of the connector and configured and arranged to couple the contacts of the lead to the electronic subassembly.

11. The stimulation device of claim 10, wherein the unitary body further defines a stop pocket at an end of the hollow region.

12. The stimulation device of claim 10, wherein the connector pockets are spaced-apart at substantially uniform intervals.

13. The stimulation device of claim 10, further comprising a connector block coupled to the unitary body.

14. The stimulation device of claim 10, further comprising a plurality of conductors that couple the electronic subassembly to the conductive contacts.

15. A method of making a stimulation device that provides electrical pulses to a tissue comprising:

forming a connector comprising a unitary body defining a hollow center region configured and arranged to receive a proximal contact portion of a lead, wherein the unitary body further defines within the hollow center region a plurality of spaced-apart connector pockets, wherein each connector pocket defines an opening through the unitary body, and the unitary body further defining within the hollow center region a plurality of seal features disposed between the connector pockets;

disposing a plurality of conductive contacts in the openings through the unitary body and entirely in the connector pockets except for a part, if any, of the contacts which protrude through the openings; and coupling contacts on a lead to an electronic subassembly through the connector and conductive contacts.

16. The method of claim 15, wherein the connector is formed by molding, and wherein forming a connector comprises:

disposing mold insert pieces in a mold frame;

forming a unitary body around the mold insert pieces; and removing the mold insert pieces from the unitary body formed around the mold insert pieces.

17. The method of claim 16, wherein disposing told insert pieces in a mold frame comprises disposing mold insert pieces in a mold frame using a locating feature.

18. The method of claim 15, wherein disposing a plurality of the conductive contacts in the openings through the unitary body comprises swelling the material used to form the unitary body.

19. The method of claim 15, further comprising coupling a connector block to the unitary body.

20. The method of claim 15, wherein coupling a lead to an electronic subassembly comprises coupling the lead to the electronic subassembly via a plurality of conductors.

* * * * *